United States Patent
Borzatta et al.

(10) Patent No.: US 10,537,100 B2
(45) Date of Patent: Jan. 21, 2020

(54) SUBSTITUTED METHYLENEDIOXYBENZYL COMPOUNDS AND THEIR USE AS SYNERGISTS

(71) Applicants: Endura SPA, Bologna (IT); AGCHEM ACCESS LTD, Norwich, Norfolk (GB)

(72) Inventors: Valerio Borzatta, Bologna (IT); Elisa Capparella, Ravenna (IT); Francesco Tozzi, Bologna (IT); Graham David Moores, Stevenage (GB); János Szilágyi, Budapest (HU); László Barnabás Takács, Budapest (HU); József Schmidt, Bicske (HU); Mark Johnston, Manchester (GB)

(73) Assignees: Endura SPA, Bologna (IT); AGCHEM ACCESS LTD, Norwich, Norfolk (GB)

( * ) Notice: Subject to any disclaimer, the term of this patent is extended or adjusted under 35 U.S.C. 154(b) by 0 days.

(21) Appl. No.: 15/758,753

(22) PCT Filed: Sep. 7, 2016

(86) PCT No.: PCT/EP2016/071017
§ 371 (c)(1),
(2) Date: Mar. 9, 2018

(87) PCT Pub. No.: WO2017/042184
PCT Pub. Date: Mar. 16, 2017

(65) Prior Publication Data
US 2019/0037845 A1 Feb. 7, 2019

(30) Foreign Application Priority Data
Sep. 9, 2015 (EP) .................................... 15184405

(51) Int. Cl.
| | | |
|---|---|---|
| *A01N 43/30* | (2006.01) | |
| *A01N 47/40* | (2006.01) | |
| *A01N 51/00* | (2006.01) | |
| *A01N 53/00* | (2006.01) | |
| *A61K 31/357* | (2006.01) | |
| *A61P 33/14* | (2006.01) | |

(52) U.S. Cl.
CPC ............ *A01N 43/30* (2013.01); *A61K 31/357* (2013.01); *A61P 33/14* (2018.01); *A01N 47/40* (2013.01); *A01N 51/00* (2013.01); *A01N 53/00* (2013.01); *A01N 2300/00* (2013.01)

(58) Field of Classification Search
None
See application file for complete search history.

(56) References Cited

FOREIGN PATENT DOCUMENTS

| | | |
|---|---|---|
| WO | 2012123714 A1 | 9/2012 |
| WO | 2013135806 A1 | 9/2013 |
| WO | 2014147387 A1 | 9/2014 |

OTHER PUBLICATIONS

Broadbent et al., Synergistic abilities of esters of 6-n-propylpiperonylic acid with pyrethrins and Neopynamin, Pyrethrum Post (1971), 11(2), 63-5, 68. (Year: 1971).*
International Preliminary Report on Patentability of PCT/EP2016/071017 dated Nov. 10, 2017.
International Search Report and Written Opinion of PCT/EP2016/071017 dated Nov. 17, 2016.
Kodwo D. Ninsin, et al. "Synergism and stability of acetamiprid resistance in a laboratory colony of Plutella xylostella", Pest Management Science, vol. 61, No. 8, Aug. 1, 2005, pp. 723-727.
Pap L., et al., "Comparative evaluation of new synergists containing a butynyl-type synergophore group and piperonyl butoxide derivatives," Pest Management Science, vol. 57, No. 2, Feb. 1, 2001 pp. 186-190.
Preston C. et al., "Multiple mechanisms and multiple herbicide resistance in lolium rigidum," in "Molecular Genetics and Evolution of Pesticide Resistance", Sep. 27, 1996, American Chemical Society, vol. 645, pp. 117-129.
Andersen, J.F., et al., "Substrate Specificity for the epoxidation of terpenoids and active site topology of house fly cytochrome P450 6A1", Chem. Res. Toxicol. 1997, 10, 156-164.
Cornel et al., "High level methoprene resistance in the mosquito *Ochlerotatus nigromaculis* (Ludlow) in Central California)", Pest Manag Sci 58:791-798 (online 2002).
Office Action of corresponding EP application dated Apr. 3, 2019.

* cited by examiner

*Primary Examiner* — Alton N Pryor
(74) *Attorney, Agent, or Firm* — Silvia Salvadori, P.C.; Silvia Salvadori

(57) ABSTRACT

The present invention relates to a pesticide composition comprising at least one pesticidal active ingredient and at least one methylendioxyphenyl derivative compound of Formula (I), wherein $R_1$ is a linear $(C_4\text{-}C_6)$alkyl.

12 Claims, No Drawings

SUBSTITUTED METHYLENEDIOXYBENZYL COMPOUNDS AND THEIR USE AS SYNERGISTS

This application is a U.S. national stage of PCT/EP2016/071017 filed on 7 Sep. 2016, which claims priority to and the benefit of European Application No. 15184405.7 filed on 9 Sep. 2015, the contents of which are incorporated herein by reference in their entireties.

FIELD OF INVENTION

The invention concerns substituted methylenedioxybenzyl compounds and their uses as synergists of pesticide active ingredients.

The work leading to this invention has received funding from the European Union Seventh Framework Programme (FP7/2007-2013) under grant agreement n.605740.

STATE OF THE ART

Compounds which are no toxic or only slightly toxic against pests, but in combination with active ingredients can produce a new pesticide, having an effectiveness significantly greater than the sum of the components when used separately, are named synergists.

These compounds may in principle act in several ways, but one the main mechanism is reported by interacting with the metabolism of the active substance. Metabolism can proceed through oxidative, hydrolytic, conjugative and absorption reactions and possible variations thereof.

On the basis of the discovery of synergists and of their mode of actions, a wide range research and development started from the mid 50' giving products interesting for scientific research, but only a few for market purposes.

One of the most effective and widely used synergists is represented by piperonyl butoxide (5-[2-(2-butoxyethoxy)ethoxymethyl]-6-n-propyl-1,3-benzodioxole) claimed in U.S. Pat. No. 2,550,737.

Piperonyl butoxide is claimed to give a synergistic effect in combination with pyrethrins as well as pyrethroids such as allethrin, prallethrin, tetramethrin and so on.

Other synergists have been proposed such as MGK 264 (N-2-ethylhexylbicyclo[2.2.1]-5-heptene-2,3-dicarboximide) reported by Moore J. B. in Proceed. Mid-Year Meeting, Chem. Spec. Manuf. Association (1950), (June), 72.

Among different synergists, alkynyl derivatives were cited to give synergistic effect when in composition with pyrethroids or other active ingredients against pests. These alkynyl derivatives generally belong to two different families, being the first one represented by phenyl alkynyl ethers and the second one by benzyl alkynyl ethers.

Among the first chemical family (phenyl alkynyl ethers), phenyl-2-propynyl ethers with a synergistic effects against pests when used in combination with carbamates can be cited (Fellig J. in J. Agr. Food Chem., 18(1), 78-80,) and U.S. Pat. No. 3,423,428

Among the second family (benzyl propynyl ethers) U.S. Pat. No. 3,880,999 claims benzyl 2-propynyl ethers capable of enhancing the activity of pyrethroids and phosphoric esters.

In László Pap et al., "*Comparative evaluation of new synergists containing a butynyl-type synergophore group and piperonyl butoxide derivatives*", Pest Management Sci., 57, 186-190, (2001) the synergistic activity of substituted methylenedioxyphenyl derivatives and substituted dimethoxybenzene derivatives is studied and the 2-butynyloxymethyl group is suggested as a synergophore group, particularly for dimethoxybenzene structure, in combination with carbofuran insecticide.

In WO2012/123714 methylenedioxybenzyl derivatives in combination with neonicotinoids are described. Specifically, the methylenedioxybenzyl derivatives of the formula (I) contain a ($C_1$-$C_{12}$) alkyl group in position 6 of the methylene dioxybenzene ring and a —$CH_2$—O—CH—C≡C—$R_2$ group, wherein $R_2$ is selected from H and ($C_1$-$C_5$) alkyl. The sole compound prepared and used together with neonicotinoids in such an application is 5-(but-2-ynyloxymethyl)-6-propyl-benzo[1,3]dioxole (indicated as EN126).

In WO2014/147387 a composition comprising a herbicide and a compound of Formula (I) as in WO2012/123714 is described. Also in this application the sole compound prepared and used together with a herbicide is 5-(but-2-ynyloxymethyl)-6-propyl-benzo[1,3]dioxole (indicated as EN126).

While these methylenedioxybenzyl derivatives have shown synergistic activity with some active ingredients, it is still felt a great need for new synergistic compounds, that in combination with active ingredients show a better pesticide activity than the compounds of the prior art.

SUMMARY OF THE INVENTION

The above object has been achieved by a pesticidal composition comprising at least one pesticide active ingredient and at least one methylenedioxyphenyl derivative compound of Formula (I)

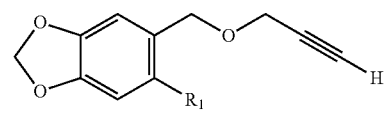

wherein $R_1$ is a linear ($C_4$-$C_6$)alkyl.

The inventors of the present invention surprisingly found out that a propargyloxy group in the methylenedioxyphenyl structure confers better synergistic activity when combined with the specific linear alkyl chain of 4-6 carbon atoms with respect to the known methylenedioxyphenyl derivative of the prior art. The selection of the two substituents in the methylenedioxyphenyl structure as per Formula (I) gave unexpected synergistic properties as it will be evident from the experimental part.

Without being bound to any theory the inventors deem that the two specific substituents in positions 5 and 6 of the methylenedioxyphenyl structure as well as the length of the alkyl chain can interact with the blockade of the enzymes, by a modulation of the binding affinity with the enzymes.

In another aspect the invention relates to the use of methylenedioxyphenyl compounds of Formula (I) as synergistic compounds of pesticide active ingredients.

Under a further aspect, the invention relates to the following specific compounds as synergists:

5-n-butyl-6-((prop-2-ynyloxy)methyl)benzo[d][1,3]dioxole, a compound of the formula (I) wherein R1 is an n-butyl substituent and 5-n-hexyl-6-((prop-2-ynyloxy)methyl)benzo[d][1,3]dioxole, a compound of the formula (I) wherein $R_1$ is an n-hexyl substituent In yet a further aspect of the invention, the invention relates to the use of the pesticide composition as pesticide.

Specifically, the invention relates also to a use of the pesticide composition for killing pests in close and open environments, more preferably in agriculture.

In yet a further aspect of the invention, the invention relates to the pesticide composition of the invention for use in veterinary medicine.

In yet a further aspect of the invention, the invention relates to the pesticide composition for use in treating pediculosis in humans.

DETAILED DESCRIPTION OF THE INVENTION

The present invention concerns a pesticide composition comprising at least one pesticidal active ingredient and at least one methylendioxyphenyl derivative compound of Formula (I)

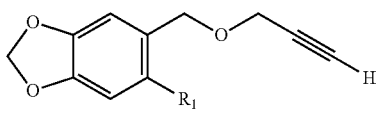

wherein $R_1$ is a linear ($C_4$-$C_6$)alkyl.

Preferably $R_1$ is n-butyl or n-hexyl, more preferably n-butyl.

Under a further aspect, the invention relates to the following specific compounds as synergists:

a) 5-n-butyl-6-((prop-2-ynyloxy)methyl)benzo[d][1,3]dioxole

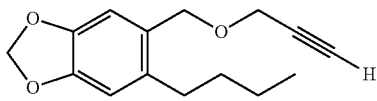 [SMILES: C#CCOCc1cc2c(cc1CCCC)OCO2]

with molecular formula $C_{15}H_{18}O_3$ and molecular weight (MW) of 246.30 Dalton, whose structure was confirmed by $^1H$ and $^{13}C$ NMR analyses.

b) 5-n-hexyl-6-((prop-2-ynyloxy)methyl)benzo[d][1,3]dioxole

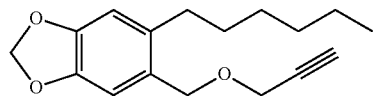 [SMILES: C#CCOCc1cc2c(cc1CCCCCC)OCO2]

with molecular formula $C_{17}H_{22}O_3$ and molecular weight (MW) of 274.35 Dalton whose structure was confirmed by $^1H$ and $^{13}C$ NMR analyses.

The pesticide composition of the present invention comprises the present compounds of the formula (I) and a pesticide active ingredient.

The ratio between the present methylenedioxybenzyl compound of the formula (I) and the pesticide active ingredient which are contained in the pesticide composition of the present invention is optionally adjustable without limitation according to the control objectives such as kinds of pests, application places, applying times, kinds of the pesticide active ingredient. Typical weight ratio of the present compound to pesticide active ingredient is from about 1:100 to about 100:1, preferably from about 1:50 to about 50:1, more preferably from 20:1 to 1:1.

Examples of the pesticide active ingredient of the present pesticide composition are:

pyrethroid compounds such as allethrin, tetramethrin, prallethrin, phenothrin, resmethrin, cyphenothrin, permethrin, cypermethrin, alpha-cypermethrin, zeta-cypermethrin, deltamethrin, tralomethrin, cyfluthrin, beta-cyfluthrin, cyhalothrin, lambda-cyhalothrin, flumethrin, imiprothrin, etofenprox, fenvalerate, esfenvalerate, fenpropathrin, silafluofen, bifenthrin, transfluthrin, flucythrinate, tau-fluvalinate, acrinathrin, tefluthrin, cycloprothrin, 2,3,5,6-tetrafluoro-4-(methoxymethyl)benzyl-(EZ)-(1RS,3RS; 1RS,3SR)-2,2-dimethyl-3-prop-1-enylcyclopropanecarboxylate, 2,3,5,6-tetrafluoro-4-methylbenzyl(EZ)-(1RS, 3RS;1RS,3SR)-2,2-dimethyl-3-prop-1-enylcycloprop anecarboxylate, 2,3,5,6-tetrafluoro-4-(methoxymethyl)benzyl(1RS,3RS;1RS,3SR)-2,2-dimethyl-3-(2-methylprop-1-enyl)cyclopropanecarboxylate, empenthrin, 2,3,5,6-tetrafluoro-4-methoxymethylbenzyl(EZ)-(1RS,3RS;1RS,3SR)-3-(2-cyan-o-1-propenyl)-2,2-dimethylcyclopr opaneca rboxylate, 2,3,5,6-tetrafluoro-4-methoxymethylbenzyl(EZ)-(1RS,3RS;1RS,3SR)-3-(2-cyan-o-2-ethoxycarbonylvinyl)-2,2-dimethylcyclopropanecarboxylate, 2,3,5,6-tetrafluoro-4-methoxymethylbenzyl(1RS,3RS;1RS,3SR)-3-(2,2-dichlor-ovinyl)-2,2-dimethylcyclopropanecarboxylate, 2,3,5,6-tetrafluoro-4-methoxymethylbenzyl(EZ)-(1RS,3RS;1 RS,3SR)-3-methoxy-iminomethyl-2,2-dimethylcyclopropanecarboxylate and 2,3,5,6-tetrafluoro-4-methoxymethylbenzyl(EZ)-(1RS,3RS;1RS,3SR)-3-(2-etho-xycarbonyl-2-fluorovinyl)-2,2-dimethylcyclopropanecarboxylate;

organic phosphorus compounds such as dichlorvos, fenitrothion, cyanophos, profenofos, sulprofos, phenthoate, isoxathion, tetrachlorvinphos, fenthion, chlorpyriphos, diazinon, acephate, terbufos, phorate, chlorethoxyfos, fosthiazate, ethoprophos, cadusafos and methidathion; carbamate compounds such as propoxur, carbaryl, metoxadiazone, fenobucarb, methomyl, thiodicarb, alanycarb, benfuracarb, oxamyl, aldicarb and methiocarb; benzoylphenylurea compounds such as lufenuron, chlorfluazuron, hexaflumuron, diflubenzuron, triflumuron, teflubenzuron, flufenoxuron, fluazuron, novaluron, triazuron and bistrifluron; juvenile hormone-like substances such as pyriproxyfen, methoprene, hydroprene and fenoxycarb;

neonicotinoid compounds such as acetamiprid, nitenpyram, thiacloprid, thiamethoxam, dinotefuran, imidacloprid and clothianidin;

phenylpyrazole compounds such as acetoprole and ethiprole;

benzoylhydrazine compounds such as tebufenozide, chromafenozide, methoxyfenozide and halofenozide;

other pesticidal active ingredients such as diafenthiuron, pymetrozine, flonicamid, triazamate, buprofezin, spinosad, emamectin benzoate, chlorfenapyr, indoxacarb MP, pyridalyl, cyromazine, fenpyroximate, tebufenpyrad, tolfenpyrad, pyridaben, pyrimidifen, fluacrypyrim, etoxazole, fenazaquin, acequinocyl, hexythiazox, clofentezine, fenbutatin oxide, dicofol, propargite, abamectin, milbemectin, amitraz, cartap, bensultap, thiocyclam, endosulfan, spirodiclofen, spiromesifen, amidoflumet and azadirachtin.

The pesticide composition of the present invention can also comprise a solid carrier, a liquid carrier and/or a gaseous carrier and, further, if necessary, excipients selected from a surfactant and other adjuvants to have a pesticide formulation.

The pesticide formulation can contain excipients to have an emulsion, an oil solution, a shampoo preparation, a flowable preparation, a powder, a wettable powder, a granule, a paste, a microcapsule, a foam, an aerosol, a carbon dioxide gas preparation, a tablet, a resin preparation, a paper preparation, a nonwoven fabric preparation, and a knitted or woven fabric preparation. These preparations may be used in the form of a poison bait, a pesticide coil, an electric pesticide mat, a smoking preparation, a fumigant or a sheet.

A preparation obtained with the pesticide composition of the present invention contains usually 0.01 to 98% by weight of the present composition with respect to the total weight of the preparation.

A solid carrier used for the pesticide formulation includes finely-divided powder or granules of clay (e.g., kaolin clay, diatomaceous earth, bentonite, Fubasami clay, acid clay, etc.), synthetic hydrated silicon oxide, talc, ceramics, other inorganic minerals (e.g., sericite, quartz, sulfur, activated carbon, calcium carbonate, hydrated silica, calcium phosphate etc.), hydroxyapatite or chemical fertilizers (e.g., ammonium sulfate, ammonium phosphate, ammonium nitrate, ammonium chloride, urea, etc.); a substance which can be sublimated and is in the solid form at normal temperature (e.g., 2,4,6-triisopropyl-1,3,5-trioxane, naphthalene, p-dichlorobenzene, camphor, adamantan, etc.); wool; silk; cotton; hemp; pulp; synthetic resins (e.g., polyethylene resins such as low-density polyethylene, straight low-density polyethylene and high-density polyethylene; ethylene-vinyl ester copolymers such as ethylene-vinyl acetate copolymers; ethylene-methacrylic acid ester copolymers such as ethylene-methyl methacrylate copolymers and ethylene-ethyl methacrylate copolymers; ethylene-acrylic acid ester copolymers such as ethylene-methyl acrylate copolymers and ethylene-ethyl acrylate copolymers; ethylene-vinylcarboxylic acid copolymers such as ethylene-acrylic acid copolymers; ethylene-tetracyclododecene copolymers; polypropylene resins such as propylene homopolymers and propylene-ethylene copolymers; poly-4-methylpentene-1, polybutene-1, polybutadiene, polystyrene; acrylonitrile-styrene resins; styrene elastomers such as acrylonitrile-butadiene-styrene resins, styrene-conjugated diene block copolymers, and styrene-conjugated diene block copolymer hydrides; fluororesins; acrylic resins such as poly(methyl methacrylate); polyamide resins such as nylon 6 and nylon 66; polyester resins such as polyethylene terephthalate, polyethylene naphthalate, polybutylene terephthalate, and polycyclohexylenedimethylene terephthalate; polycarbonates, polyacetals, polyacrylsulfones, polyarylates, hydroxybenzoic acid polyesters, polyetherimides, polyester carbonates, polyphenylene ether resins, polyvinyl chloride, polyvinylidene chloride, polyurethane, and porous resins such as foamed polyurethane, foamed polypropylene, or foamed ethylene, etc.), glasses, metals, ceramics, fibers, cloths, knitted fabrics, sheets, papers, yarn, foam, porous substances, and multifilaments.

A liquid carrier includes, for example, aromatic or aliphatic hydrocarbons (e.g., xylene, toluene, alkylnaphthalene, phenylxylylethane, kerosene, gas oil, hexane, cyclohexane, etc.), halogenated hydrocarbons (e.g., chlorobenzene, dichloromethane, dichloroethane, trichloroethane, etc.), alcohols (e.g., methanol, ethanol, isopropyl alcohol, butanol, hexanol, benzyl alcohol, ethylene glycol, etc.), ethers (e.g., diethyl ether, ethylene glycol dimethyl ether, diethylene glycol monomethyl ether, diethylene glycol monoethyl ether, propylene glycol monomethyl ether, tetrahydrofuran, dioxane, etc.), esters (e.g., ethyl acetate, butyl acetate, etc.), ketones (e.g., acetone, methyl ethyl ketone, methyl isobutyl ketone, cyclohexanone, etc.), nitriles (e.g., acetonitrile, isobutyronitrile, etc.), sulfoxides (e.g., dimethyl sulfoxide, etc.), amides (e.g., N,N-dimethylformamide, N,N-dimethylacetamide, cyclic imides (e.g. N-methylpyrrolidone) alkylidene carbonates (e.g., propylene carbonate, etc.), vegetable oil (e.g., soybean oil, cottonseed oil, etc.), vegetable essential oils (e.g., orange oil, hyssop oil, lemon oil, etc.), and water.

A gaseous carrier includes, for example, butane gas, flon gas, liquefied petroleum gas (LPG), dimethyl ether, and carbon dioxide gas.

A surfactant includes, for example, alkyl sulfate ester salts, alkyl sulfonates, alkyl aryl sulfonates, alkyl aryl ethers and polyoxyethylenated products thereof, polyethylene glycol ethers, polyvalent alcohol esters and sugar alcohol derivatives.

Other adjuvants for formulation include binders, dispersants and stabilizers, specifically, for example, casein, gelatin, polysaccharides (e.g., starch, gum arabic, cellulose derivatives, alginic acid, etc.), lignin derivatives, bentonite, sugars, synthetic water-soluble polymers (e.g., polyvinyl alcohol, polyvinylpyrrolidone, polyacrylic acid, etc.), PAP (acidic isopropyl phosphate), BHT (2,6-di-t-butyl-4-methylphenol), BHA (a mixture of 2-t-butyl-4-methoxyphenol and 3-t-butyl-4-methoxyphenol), vegetable oils, mineral oils, fatty acids and fatty acid esters.

According to the invention the pesticide composition contain at least one methylenedioxyphenyl derivative compound as synergistic compound. Other synergists can be present in the composition, also those known in the art such as piperonyl butoxide, MGK 264 and Verbutin The present compound can be used in pest control by applying an effective amount of the present compound and a pesticide active ingredient, i.e. the present pesticidal composition to pests directly and/or a biotope thereof (e.g., plants, animals, soil, etc.).

Therefore, in yet a further aspect of the invention, the invention relates to the pesticide composition of the invention for use in veterinary medicine and in yet a further aspect of the invention, the invention relates to the pesticide composition for use in treating pediculosis in humans.

When the pesticide composition of the present invention is used for controlling pests in agriculture and forestry, the application amount is usually 1 to 5,000 g/ha, preferably 10 to 800 g/ha of total amount of the present active ingredient.

When the pesticide composition of the present invention is the form of an emulsion, a wettable powder, a flowable agent, or a microcapsule, it is usually used after dilution with water so as to have the present active ingredient concentration of 0.01 to 1,000 ppm. When the pesticide composition of the present invention is the form of an oil solution, a powder or a granule, it is usually used as it is.

These preparations as it is may be sprayed as they are to plants to be protected from pests, or may be diluted with water and then sprayed to a plant to be protected from pests. Soil can be treated with these preparations to control pests living in the soil. Seedbeds before planting or planting holes or plant feet in planting can be also treated with these preparations. Further, a sheet preparation of the pesticide composition of the present invention may be applied by winding around plants, disposing in the vicinity of plants, laying on the soil surface at the plant feet or the like.

When the pesticide composition of the present invention is used for a control of pests of epidemic, the application amount is usually 0.001 to 100 mg/m$^3$ of total amount of the present active ingredient for application to space, and 0.001 to 1,000 mg/m$^2$ of total amount of the present active ingredient for application to a plane. When the pesticide composition of the present invention is the form of an emulsion, a wettable powder or a flowable agent, it is usually applied after dilution with water so as to have the present active ingredient concentration of 0.001 to 10,000 ppm, preferably 0.01 to 1,000 ppm. When the pesticide composition of the present invention is in the form of an oil solution, an aerosol, a smoking preparation or a poison bait, it is usually applied as it is. The pesticide composition in the form of pesticide coil, or an electric pesticide mat is applied by emitting the present active ingredient by heating depending on its form. The pesticide composition in the form of a resin preparation, a paper preparation, a tablet, a nonwoven fabric preparation, a knitted or woven fabric preparation or a sheet preparation can be applied, for example, by leaving the preparation as it is in a space to be applied and by sending air to the preparation.

A space to which the pesticide composition of the present invention is applied for prevention of epidemics includes, for example, a closet, a Japanese-style closet, a Japanese-style chest, a cupboard, a lavatory, a bathroom, a lumber room, a living room, a dining room, a warehouse, and the car inside. The pesticide composition may be also applied in outdoor open space.

When the pesticide composition of the present invention is used for controlling parasites living outside of a livestock such as a cow, a horse, a pig, a sheep, a goat or a chicken, or a small animal such as a dog, a cat, a rat or a mouse, it can be used for said animal by a known method in the veterinary field. Specifically, when systemic control is intended, the pesticide composition is administered, for example, as a tablet, a mixture with feed, a suppository or an injection (e.g., intramuscularly, subcutaneously, intravenously, intraperitoneally, etc.). When non-systemic control is intended, a method of using the pesticide composition of the present invention includes spraying, pour-on treatment or a spot-on treatment with the pesticide composition in the form of an oil solution or an aqueous liquid, washing an animal with the pesticide composition in the form of a shampoo preparation, and attachment of a collar or a ear tag made of the pesticidal composition in the form of a resin preparation to an animal. When administered to an animal, total amount of the present active ingredient is usually in the range of 0.01 to 300 mg per 1 kg body weight of the animal.

Pests against which the pesticide composition of the present invention has controlling effect include harmful arthropods such as insects and mites. More specifically, examples thereof are listed below.

Hemiptera; Delphacidae such as *Laodelphax striatellus, Nilaparvata lugens, Sogatella furcifera* and the like; Deltocephalidae such as *Nephotettix cincticeps, Nephotettix virescens* and the like; Aphididae such as *Aphis gossypii, Myzus persicae* and the like, Pentatomidae and Alydidae, such as *Nezara antennata, Riptortus clavetus, Eysarcoris lewisi, Eysarcoris parvus, Plautia stali, Halyomorpha mista* and the like, Aleyrodidae such as *Trialeurodes vaporariorum, Bemisia argentifolii* and the like, Diaspididae, Coccidae and Margarodidae, such as *Aonidiella aurantii, Comstockaspis perniciosa, Unaspis citri, Ceroplastes rubens, Icerya purchasi* and the like, Tingidae, Cimicidae such as *Cimex lectularius* and the like, Psyllidae, and the like; Lepidoptera; Pyralidae such as *Chilo suppressalis, Cnaphalocrocis medinalis, Notarcha derogata, Plodia interpunctella* and the like, Noctuidae such as *Spodoptera litura, Pseudaletia separata, Trichoplusia* spp., *Heliothis* spp., *Helicoverpa* spp. and the like, Pieridae such as *Pieris rapae* and the like, Tortricidae such as *Adoxophyes* spp., *Grapholita molesta, Cydia pomonella* and the like, Carposinidae such as *Carposina niponensis* and the like, Lyonetiidae such as *Lyonetia* spp. and the like, Lymantriidae such as *Lymantria* spp., *Euproctis* spp. and the like, Yponomeutidae such as *Plutella xylostella* and the like, Gelechiidae such as *Pectinophora gossypiella* and the like, Arctiidae such as *Hyphantria cunea* and the like, Tineidae such as *Tinea translucens, Tineola bisselliella* and the like; Diptera: Culicidae such as *Culex pipiens pallens, Culex tritaeniorhynchus, Culex quinquefasciatus* and the like, *Aedes* spp. such as *Aedes aegypti, Aedes albopictus* and the like, *Anopheles* spp. such as *Anopheles sinensis* and the like, Chironomidae, Muscidae such as *Musca domestica, Muscina stabulans* and the like, Calliphoridae, Sarcophagidae, Fanniidae, Anthomyiidae such as *Delia latura, Delia antiqua* and the like, Tephritidae, Drosophilidae, Phoridae such as *Megaselia spiracularis* and the like, sychodidae such as *Clogmia albipunctata* and the like, Simuliidae, Tabanidae, *Stomoxys* spp., Agromyzidae, and the like; Coleoptera: rn rootworms such as *Diabrotica virgifera virgifera, Diabrotica undecimpunctata howardi* and the like, Scarabaeidae such as *Anomala cuprea, Anomala rufocuprea* and the like, Rhynchophoridae, Curculionidae and Bruchidae, such as *Sitophilus zeamais, Lissorhoptrus oryzophilus, Callosobruchus chienensis* and the like, Tenebrionidae such as *Tenebrio molitor, Tribolium castaneum* and the like, Chrysomelidae such as *Oulema oryzae, Aulacophora femoralis, Phyllotreta striolata, Leptinotarsa decemlineata* and the like, Dermestidae such as *Dermestes maculates* and the like, Anobiidae, *Epilachna* spp. such as *Epilachna vigintioctopunctata* and the like, Lyctidae, Bostrychidae, Ptinidae, Cerambycidae, *Paederus fuscipes*, and the like; Blattaria: *Blattella germanica, Periplaneta fuliginosa, Periplaneta americana, Periplaneta brunnea, Blatta orientalis* and the like; Thysanoptera: *Thrips palmi, Thrips tabaci, Frankliniella occidentalis, Frankliniella intonsa* and the like; Hymenoptera: Formicidae such as *Monomorium pharaosis, Formica fusca japonica, Ochetellus glaber, Pristomyrmex pungens, Pheidole noda*, and the like; Vespidae, Bethylidae, Tenthredinidae such as *Athalia japonica*, and the like; Orthoptera: Gryllotalpidae, Acrididae, and the like; Aphaniptera: *Ctenocephalides felis, Ctenocephalides canis, Pulex irritans, Xenopsylla cheopis*, and the like; Anoplura: *Pediculus humanus corporis, Phthirus pubis, Haematopinus eurysternus, Dalmalinia ovis*, and the like; Isoptera: Subterranean termites such as *Reticulitermes speratus, Coptotermes formosanus, Reticulitermes flavipes, Reticulitermes hesperus, Reticulitermes virginicus, Reticulitermes tibialis, Heterotermes aureus*, and the like, Dry wood termites such as Incisitermes minor, and the like, Damp wood termites such as *Zootermopsis nevadensis*, and the like; Acarina: Tetranychidae such as *Tetranychus urticae, Tetranychus kanzawai, Panonychus citri, Panonychus ulmi, Oligonychus* spp. and the like, Eriophyidae such as *Aculops pelekassi, Aculus schlechtendali*, and the like, Tarsonemidae such as *Polyphagotarsonemus latus*, and the like, Tenuipalpidae, Tuckerellidae, Ixodidae such as *Haemaphysalis longicornis, Haemaphysalis flava, Dermacentor variabilis, Ixodes ovatus, Ixodes persulcatus, Ixodes scapularis, Boophilus microplus, Amblyomma americanum, Rhipicephalus sanguineus*, and the like, Acaridae such as *Tyrophagus putrescentiae*, and the like, Epidermoptidae such as *Dermatophagoides farinae, Dermatophagoides ptrenyssnus*, and the like, Cheyletidae such as *Cheyletus eruditus, Cheyletus malaccensis, Cheyletus moorei, Ornithoonyssus bacoti, Ornithonyssus sylvairum* and the like, Dermanyssidae such as *Dermanyssus gallinae*, and the like, Trombiculidae such as *Leptotrombidium akamushi*, and the like; Araneae: *Chira-*

*canthium japonicum, Latrodectus hasseltii*, and the like; Chilopoda: *Thereuonema hilgendorfi, Scolopendra subspinipes*, and the like; Diplopoda: *Oxidus gracilis, Nedyopus tambanus*, and the like; Isopoda: *Armadillidium vulgare*, and the like; Gastropoda: *Limax marginatus, Limax flavus*, and the like.

The pesticide compositions of the present invention are preferably suitable for agriculture and for professional pest control operators.

In particular the pesticide composition of the present invention are suitable for the following insect orders: Hemiptera, Diptera, Blattaria, Thysanoptera, Isoptera, and Acarina.

The invention will be now detailed by means of the following examples relating to the preparation of some invention synergistic compounds and to the evaluation of their activity Experimental Parts Preparation of the Compounds of Formula (I)

Example 1

Synthesis of 5-n-hexyl-6-((prop-2-ynyloxy)methyl) benzo[d][1,3]dioxole a) Synthesis of 5-n-hexyl-benzo[d][1,3]dioxole The compound was prepared following the procedure reported in U.S. Pat. No. 6,342,613 starting from 175 g (0.8 mol) of hexanoic anhydride (purity 98%), 153 g (1.25 mol) of benzo[d][1,3]dioxole and 10.9 g (0.08 mol) of zinc chloride. The reaction was carried out at 100° C. for 6 hrs, cooled down to room temperature, washed with acidic water and the organic phase separated off. The organic phase was washed twice with water, dried on anhydrous sodium sulphate, filtered, distilled u.v (55° C./150 Pa) and subsequently at 133° C./30 Pa, obtaining 137.4 g of an oil product, that was hydrogenated on Pd/C at 130° C./0.5 MPa for 7 hrs. After filtration of the catalyst, 131 g of an oil product is obtained whose NMR ($^1$H and $^{13}$C) and GC-MS analyses conform to the structure $^1$H NMR (400 MHz, CDCl$_3$):
δ=0.877 (3H, t, J=7.6 Hz (CH$_3$)); 1.300 (6H, m, (CH$_2$)); 1.551 (2H, quint, J=7.6 Hz (CH$_2$)); 2.505 (2H, t, J=7.6 Hz (CH$_2$)); 5.881 (2H, s, (CH$_2$)); 6.600 (1H, dd, J$_{5-7}$=1.6 Hz (ArCH); 6.660 (1H, d, J$_{7-5}$=1.6 Hz (ArCH); 6.701 (1H, d, J$_{4-5}$=8 Hz, (ArCH).

$^{13}$C NMR, CDCl$_3$, 100 MHz:
δ=14.040 (CH$_3$); 22.580 (CH$_2$); 28.840 (CH$_2$); 31.698 e 31.699 (CH$_2$); 35.665 (CH$_2$); 100.611 (CH$_2$); 107.948 (ArCH); 108.799 (ArCH); 120.952 (ArCH); 136.764 (ArC); 145.355 (ArC); 147.422 (ArC).

GC-MS (EI) m/z (%): 204 (60) [M+], 146 (3), 133 (100), 149 (100), 115 (4), 91 (6), 77 (10).

b) Synthesis of 5-n-hexyl-6-((prop-2-ynyloxy) methyl)benzo[d][1,3]dioxole

In a flask equipped with a stirrer 48.5 g (0.24 mol) of 5-n-hexyl-benzo[d][1,3]dioxole were added with 12.9 g (0.43 mol) of paraformaldehyde, 1.64 g (0.012 mol) of zinc chloride and 120 g (1.20 mol) of HCl 37%. The mixture was the heated to 60° C. and maintained under stirring for further 23 hrs. The solution was then cooled down to 30° C., added with 50 ml of toluene and the organic phase was separated off. The organic phase was then added slowly to a mixture prepared by reacting 24.5 g (0.432 mol) of propargyl alcohol and 19.2 g (0.48 mol) of solid sodium hydroxide at 55° C. for half an hour. After the addition the mixture is maintained under stirring at 60° C. for 4 hrs, cooled down to room temperature and added with 50 ml of NaCl 10% aqueous solution under stirring. The organic solution is then separated off and the solvent evaporated u.v (25° C./500 Pa). The oil residue was then distilled at 150° C./30 Pa obtaining 34.4 g of an oil product whose NMR ($^1$H and $^{13}$C) and CG-MS analyses conform to the structure $^1$H NMR (400 MHz, CDCl$_3$):
δ=0.88-0.92 (m, 3H, CH$_3$), 1.29-1.38 (m, 6H, CH$_2$), 1.55 (m, 2H, CH$_2$), 2.48 (t, J=2.40 Hz, 1H, CH), 2.59 (t, J=8.00 Hz, 2H, CH$_2$), 4.16 (d, J=2.40 Hz, 2H, CH$_2$), 4.52 (s, 2H, CH$_2$), 5.90 (s, 2H, CH$_2$), 6.68 (s, 1H, ArCH), 6.84 (s, 1H, Ar—CH).

$^{13}$C NMR (100 MHz, CDCl$_3$):
δ=14.12 (CH$_3$), 22.64 (CH$_2$), 29.26 (CH$_2$), 31.65 (CH$_2$), 31.76 (CH$_2$), 32.37 (CH$_2$), 56.86 (CH$_2$), 69.09 (CH$_2$), 74.59 (=CH), 79.81 (≡C), 100.84 (CH$_2$), 109.53 (ArCH), 109.90 (ArCH), 127.74 (ArC), 135.8 (ArC), 145.45 (ArC), 147.36 (ArC).

GC-MS (EI) m/z (%): 274 (75) [M+], 218 (80), 175 (27), 163 (28), 149 (100), 135 (35), 115 (18), 91 (11), 77 (12).

Example 2

Synthesis of 5-n-butyl-6-((prop-2-ynyloxy)methyl) benzo[d][1,3]dioxole a) Synthesis of 5-n-butyl-benzo[d][1,3]dioxole Following the same procedure described in Example 1a), but starting from 76 g (0.48 mol) of butyric anhydride, 120.8 g (0.99 mol) of benzo[d][1,3]dioxole and 6.8 g (0.05 mol) of zinc chloride, a product was obtained that was hydrogenated at 0.5 MPa in Pd/C. After the work up the raw product was distilled u.v (61° C./50 Pa) obtaining 65 g of an oil product whose NMR ($^1$H and $^{13}$C) and GC-MS analyses conform to the structure $^1$H NMR CDCl$_3$, 400 MHz:
δ=1.006 (3H, t, J=7.6 Hz (CH$_3$)); 1.419 (2H, sest, J=7.6 Hz (CH$_2$)); 1.633 (2H, quint, J=7.6 Hz (CH$_2$)); 2.599 (2H, t, J=7.6 Hz (CH$_2$)); 5.944 (2H, s, (CH$_2$) 6.683 (1H, dd, J$_{5-4}$=8 Hz, J$_{5-7}$=1.8 Hz (ArCH); 6.749 (1H, d, J$_{7-5}$=1.8 Hz (ArCH); 6.786 (1H, d, J$_{4-5}$=8 Hz, (ArCH).

$^{13}$C NMR, CDCl$_3$, 100 MHz:
δ=13.820 (CH$_3$); 22.148 (CH$_2$); 33.825 (CH$_2$); 35.283 (CH$_2$); 100.552 (CH$_2$); 107.875 (ArCH); 108.733 (ArCH); 120.901 (ArCH); 136.610 (ArC); 145.355 (ArC); 147.415 (ArC).

GC-MS (EI) m/z (%): 176 (22) [M+], 133 (100)

b) Synthesis of 5-n-butyl-6-((prop-2-ynyloxy) methyl)benzo[d][1,3]dioxole

Following the same procedure described in Example 1b), but starting from 60.6 g (0.33 mol) of 5-n-butyl-benzo[d][1,3]dioxole, 16.6 g (0.55 mol) of paraformaldehyde, 148 g (1.79 mol) of hydrochloric acid 37% and 2.2 g (0.016 mol) of zinc chloride were reacted to give an intermediate product that was not isolated and reacted with 15.14 g (0.27 mol) propargyl alcohol and 13.5 g (0.34 mol) of sodium hydroxide. After the separation of the organic phase and the solvent evaporation u.v. (25° C./500 Pa)., an oil residue was obtained that was distilled u.v. (120°-125° C./10 Pa) and whose NMR ($^1$H and $^{13}$C) and GC-MS analyses conform to the structure.

$^1$H NMR (400 MHz, CDCl$_3$):

δ=0.88-0.92 (m, 3H, CH$_3$), 1.29-1.38 (m, 6H, (CH$_2$)), 1.55 (m, 2H, CH$_2$), 2.48 (t, J=2.40 Hz, 1H, CH), 2.59 (t, J=8.00 Hz, 2H, CH$_2$), 4.16 (d, J=2.40 Hz, 2H, CH$_2$), 4.52 (s, 2H, CH$_2$), 5.90 (s, 2H, CH$_2$), 6.68 (s, 1H, ArCH), 6.84 (s, 1H, ArCH).

$^{13}$C NMR (100 MHz, CDCl$_3$):

δ=14.12 (CH$_3$), 22.64 (CH$_2$), 29.26 (CH$_2$), 31.65 (CH$_2$), 31.76 (CH$_2$), 32.37 (CH$_2$), 56.86 (CH$_2$), 69.09 (CH$_2$), 74.59 (≡CH), 79.81 (≡C), 100.84 (CH$_2$), 109.53 (Ar—CH), 109.90 (Ar—CH), 127.74 (ArC), 135.98 (ArC), 145.45 (ArC), 147.36 (ArC).

GC-MS (EI) m/z (%): 246 (87) [M+], 190 (100), 175 (21), 163 (83), 149 (93), 145 (27), 135 (29), 115 (18), 91 (11), 77 (13).

Example 3

Inhibition of Oxidase Enzymes by the Synergists in *Bemisia tabaci* and *Myzus persicae*

Ability of the synergists of the invention to inhibit oxidative enzymes (P450), a major mechanism conferring resistance to xenobiotics, was measured using recombinant enzymes corresponding to CYP6CY3 from *Myzus persicae* and CYP6CM1 from *Bemisia tabaci*.

The following synergists were tested in comparison with piperonyl butoxide (PBO):

5-n-butyl-6-((prop-2-ynyloxy)methyl)benzo[d][1,3]dioxole
the compound prepared in Example 2

5-n-hexyl-6-((prop-2-ynyloxy)methyl)benzo[d][1,3]dioxole
the compound prepared in Example 1

CYP6CM1

Substrate used was 7-ethoxycoumarin for inhibition assays as described by Ulrich and Weber (1972) and adapted to microplate format as described by De Sousa et al. (1995). This method had successfully been used previously to characterise inhibition by some piperonyl butoxide analogues against microsomal preparations from whole insects (Moores et al. 2009)

For inhibition assays, stock solutions of the compounds of Example 1 and Example 2 (10 mM) were prepared in acetone. Diluted recombinant enzyme (50 µL) was mixed with 3 µL of the above mentioned compound stock solutions, with acetone only used as a control. After 10 min incubation at room temperature, 80 µL of 0.125 mM 7-ethoxycoumarin was added, followed by 10 µL 9.6 mM NADPH (nicotinamide adenine dinucleotide phosphate) in 0.1 M sodium phosphate, pH 7.8, and O-deethylation activity monitored as above. A PBO solution (10 mM) was prepared in the same way as a comparison.

The results are reported below in the table 1

TABLE 1

| *Bemisia tabaci* CYPCM1 percentage of activity remaining | | |
| --- | --- | --- |
| Compound | % activity remaining | SEM |
| Compound of example 2 | 53.48 | 3.30 |
| Compound of example 1 | 85.19 | 3.89 |
| PBO | 106.49 | 4.50 |

The compounds of Examples 1 and 2 therefore show an inhibition activity better than PBO being the percentage of the remaining activity of the enzyme less when the synergists of the invention were used instead of using PBO.

CYP6CY3

For CYP6CY3, 7-ethoxycoumarin was not an appropriate substrate and MFC (7-methoxy-4-trifluoromethylcoumarin) was utilised instead. MFC was dissolved in dimethylsulfoxide to make a 20 mM stock solution and diluted by the addition of 0.1 M sodium phosphate buffer, pH 7.8, to give a concentration of 0.5 mM. Recombinant enzyme (10 µL) was added to separate wells of a microplate as before and diluted to 50 µL with 0.1 M phosphate buffer pH 7.6, followed by the addition of 80 µL of 0.5 mM MFC. The microplate was incubated for 5 min at 30° C., and the reaction was initiated by the addition of 10 µL of 9.6 mM NADPH in 0.1 M sodium phosphate, pH 7.8. Enzyme activity was read in a Spectramax Gemini EM for 60 min, with readings taken every 2 min, using an excitation wavelength of 410 nm and an emission wavelength of 510 nm, with a 495 nm cut-off filter. The rate (FU min$^{-1}$) was calculated by the integrated software, Softmax Pro v.5.4. as before.

For inhibition assays, stock solutions of the compounds of Example 1 and 2 (0.1 mM) were prepared in acetone. Dilute recombinant enzyme (50 µL) was mixed with 3 µL of stock solutions, with acetone only used as a control. After 10 min incubation at room temperature, 80 µL of 0.5 mM MFC was added, followed by 10 µL of 9.6 mM NADPH in 0.1 M sodium phosphate, pH 7.8. Enzyme activity remaining was then monitored as above. A PBO solution (10 mM) was prepared in the same way as a comparison.

The results are reported below in the table 2

TABLE 2

| *Myzus persicae* CYP6CY3 percentage of activity remaining | | |
| --- | --- | --- |
| Compound | % activity remaining | sem |
| Compound of Example 2 | 4.04 | 0.22 |
| Compound of Example 1 | 8.51 | 0.20 |
| PBO | 10.69 | 1.28 |

The compounds of Examples 1 and 2 therefore show an inhibition activity better than PBO being the percentage of the remaining activity of the enzyme less when the synergists of the invention were used instead of using PBO.

Example 4

Inhibition of Esterase Enzymes by Synergists in *Myzus persicae*

Inhibition of esterase activity cannot be measured by simple colourimetric assays using routine model substrates, as the synergist does not bind at the active site (Philippou et al., 2013). It was envisaged, therefore, that the 'esterase interference assay' (Khot et al., 2008) would be utilized for the purified esterases from aphids. Various esterase substrates were assessed to find one suitable of monitoring inhibition in an insect homogenate. The *Myzus persicae* resistance associated esterase, FE4, was used.

FE4

Initially the esterase interference assay was carried out, as being the 'absolute' protocol for characterising interactions between the compounds of Example 1 and Example 2 and FE4. However, since this is a protracted method, and it would not be applicable for the *B. tabaci* esterases, a selection of products already reported in the literature were used to compare the interference assay and the use of a model substrate.

From the literature (Philippou et al., 2013) it is known that 1-naphthyl acetate is not suitable for this assay. Instead, 4-nitrophenyl acetate was used. A 10 mM pNA stock was prepared in acetone and added to 0.02 M phosphate buffer pH 7.0 (final concentration 2 mM). The comparison was made with 6 analogues of variable efficacy.

The result of this relatively high-throughput method was found to rank the products identically to the interference assay, so this method was used for further analysis of FE4 interactions.

For the assay 10 μL of purified FE4 was diluted to a total volume of 50 μL by the addition of 0.02 M phosphate buffer, pH 7.0 in individual wells of a microplate (maxisorb, NUNC). To each well, 2.5 μL of 10 mM of the compound of Example 1 and of Example 2 in acetone was added and incubated for 10 mins, with acetone only used as a control. Following incubation, 100 μL of 0.02 phosphate buffer, pH 7.0 and 100 μL of 2 mM 4-nitrophenyl acetate was added (final volume in well 250 μL, final substrate concentration 0.8 mM). Enzyme activity was read at 405 nm in a Spectramax Tmax for 5 min, with readings taken every 5 s. The rate (mOD min$^{-1}$) was calculated by the integrated software, Softmax Pro v.5.4. A PBO solution (10 mM) was prepared in the same way as a comparison.

The results of the percentage of the activity remaining is reported in the table 3 below.

TABLE 3

Myzus persicae esterases - percentage of the activity remaining FE4

| Compound | % activity remaining | sem |
|---|---|---|
| Compound of Example 2 | 28.74 | 1.37 |
| Compound of Example 1 | 23.11 | 0.55 |
| PBO | 45.78 | 1.52 |

The compounds of Examples 1 and 2 therefore show an inhibition activity better than PBO being the percentage of the remaining activity of the enzyme less when the synergists of the invention were used instead of using PBO.

Example 5

Contact Test on Treated Surfaces for the Determination of the Efficacy of the Synergists in Combination with an Insecticide on Musca domestica Laboratory bred Musca domestica species, 4-5 days old mixed sex imagoes derived from a field collected strain were assayed for the test. 1000 ml of test solutions were prepared diluting in water 6.06 grams of cypermethrin commercial formulation, equivalent to 0.224 g of cypermethrin per liter of insecticidal solution and a suitable amount of synergist such as to have a ratio between cypermethryn and synergists=1:13. The synergists were formulated in the form of emulsified concentrate (EC). The following amount of the formulations of synergist EC were added to the above described insecticidal solution of cypermethrin.

3.83 g of EC formulation containing 77.1% (w/w) of the compound of Example 2 (5-n-butyl-6-((prop-2-ynyloxy)methyl)benzo[d][1,3]dioxole)

3.57 g of EC formulation containing 83% (w/w) of the comparison compound 5-(but-2-ynyloxymethyl)-6-n-propyl-benzo[1,3]dioxole (EN126) corresponding to 2.95 g of the compound of the invention and of the comparison product per liter of test formulation The comparison product 5-(but-2-ynyloxymethyl)-6-n-propyl-benzo[1,3]dioxole (EN126) was prepared as described in EP2683236.

1 ml of each test formulation was applied to each individual grass surface of 100 cm$^2$ by means of a hand held pump sprayer on a scale measuring by 2 decimal precision, being the acceptable limit of divergence: +/−10%. The treated glass surfaces were left at room temperature for 24 hours after treatment and prior to be used. 40 mixed sex Musca domestica imagoes (20 males and 20 females) were selected and placed into a 500 cm$^3$ glass cylinders covered with an untreated glass surface until the start of the study. Five replicates were executed, altogether 200 houseflies (100 males and 100 females) were used per test formulation. At the beginning of the test, the untreated glass covering the glass cylinder was replaced with a glass surface treated with the test formulation. The exposure time was 30 minutes. After this period of time, the treated glass surfaces were removed and replaced with untreated ones. During the test water and food (water/sugar solution) were provided to the test insect inside the glass cylinders In parallel with the test, the mortality of flies in an untreated control replicate was determined using the same conditions and methods. Throughout the control test, non-treated glass surfaces covered the glass cylinders. The maximum mortality rate allowed within the control group to consider the test representative was 10% after 24 hours. If above this value, the test was not considered representative and was repeated. During the trials, no deviance has been noted.

The test conditions were as follows:
temperature: 23-25° C.
relative humidity: min. 60%
light regime: 12 hrs dark/12 hrs natural illumination.

The reading intervals of the number of knocked down flies were: 10-20-30-40-50-60-90-120-180 minutes. Mortality was determined after 24 hours.

The efficacy was calculated according the following formula $$\text{Efficacy \%} = \frac{\text{Mortality of treated sample(\%)} - \text{Mortality of control(\%)} \times 100}{100 - \text{Mortality of control(\%)}}$$

The results are reported in the following Table 4

TABLE 4

| Test formulation | | Cypermethrin 6.06 g/l — | Cypermethrin 6.06 g/l + EN 126 EC 3.57 g/l | Cypermethrin 6.06 g/l + compound of example 2 EC 3.83 g/l | Control |
|---|---|---|---|---|---|
| Reading intervals, knowck down, mortality by % | 10' | 6* | 24 | 85 | 0 |
| | 20' | 46 | 76 | 99 | 0 |
| | 30' | 68 | 93 | 99 | 0 |
| | 40' | 83 | 90 | 100 | 0 |
| | 50' | 85 | 93 | 100 | 0 |
| | 60' | 85 | 97 | 100 | 0 |
| | 90' | 82 | 96 | 100 | 0 |
| | 120' | 76 | 90 | 100 | 0 |
| | 180' | 73 | 92 | 100 | 0 |
| | 24 h | 61 | 92 | 99 | 5 |
| Efficacy % | | 58.95 | 91.58 | 98.97 | 0 |

The compound of Example 2 gives a better efficacy of the comparison product EN126 and a better knock down activity clearly notable at short times.

Example 6

Contact Test on Treated Surfaces for the Determination of the Efficacy of the Synergists in Combination with an Insecticide on *Blattella germanica*

Laboratory bred *B. germanica* species, mixed ages (pre-immaginal and imagoes) and mixed sex were assayed for the test.

An insecticide stock solution was prepared with 150 μL of cypermethrin commercial formulation and diluted to 15 μL/mL with technical acetone to a final volume of 10 mL. The solution contained 450 μg/mL of cypermethrin per liter of insecticidal solution Stock solution of the compounds of Example 1 and Example 2 were prepared dissolving around 10 mg of EC formulations containing compounds of the Example 1 and Example 2 in technical acetone to have a final concentration of 1.365 μg/mL.

The EC formulation of the compound of Example 2 contained 80.1% (w/w) of the synergist.

The EC formulation of the compound of Example 1 contained 80.5% (w/w) of the synergist.

Stock solution (1650 μL) was diluted to 2250 μL with acetone or with stock of insecticide in acetone to have respectively a final concentration of 1 g/L of synergist (as active ingredient) or 0.12 g/L of cypermethrin+1 g/L of the compounds of Example 1 and Example 2. Insecticide alone was prepared adding 600 μL of stock solution to 1650 μL of acetone.

Glass vials (internal surface 35 cm$^2$) were treated with 350 μL of insecticide solution and allowed to dry in a fume hood on a vial rotator and used as soon as the acetone was fully evaporated.

*B. germanica* specimens were introduced singly in vials. 20 specimens were tested for each combination of product. The exposure time to product residues was 30 minutes. After this duration the specimens were transferred to an untreated vial ad provided with food and water.

In parallel within the test, a control study has been set up with the same conditions and methods using acetone only treated vials.

The maximum mortality rate allowed within the control group to consider the test representative was 10% after 24 hours. If above this value, the test was not considered representative and was repeated.

During the trials, no deviance has been noted.

The test conditions were as follows:
temperature: 22-24° C. during knock down evaluation (t: 0-30'); 26° C. during mortality assessment (t: 24 h)
relative humidity: min. 60%
light regime: 8 hrs dark/16 hrs natural illumination.

The reading intervals of the number of knocked down and the number of dead insects were: 5-10-15-20-25-30 minutes. A final reading was done 24 hours after the starting of the exposure.

The calculation model of efficacy is according to Abbott's formula (Abbott W S (1925) A method for computing the effectiveness of an insecticide. J. Econ. Entomol. 18: 265-267):

$$\text{Efficacy \%} = \frac{\text{Mortality of treated sample(\%)} - \text{Mortality of control(\%)} \times 100}{100 - \text{Mortality of control(\%)}}$$

The results are reported in the following Table 5 and represent an average of 4 repetitions.

TABLE 5

| Test formulation | | Cypermethrin 120 μg/mL | Cypermethrin 120 μg/mL + Compound of Example 1 1.0 g/L | Cypermethryn 120 μg/mL + Compound of Example 2 1.0 g/L | Control |
|---|---|---|---|---|---|
| Reading intervals, knock down minutes | 5' | 0 | 0 | 0 | 0 |
| | 10' | 6.7 | 13.3 | 0 | 0 |
| | 15' | 20 | 20 | 26.7 | 0 |
| | 20' | 40 | 46.7 | 26.7 | 0 |
| | 25' | 56.7 | 60 | 46.7 | 0 |
| | 30' | 60 | 60 | 60 | 0 |
| Mortality % 24 h | | 22.9 | 70 | 70 | 0 |

The compounds of Example 1 and Example 2 show a synergist effect when mixed with the insecticide Cypermethrin.

Example 7

Contact Test on Treated Plant for the Determination of the Efficacy of the Synergists in Combination with an Insecticide on *Myzus persicae*

Laboratory bred *Myzus persicae* clone highly resistant to insecticide, derived from a field collected population after control failure, mixed age apterous parthenogenetic females adults, were assayed for the test.

Four (4) different commercially available formulated insecticides were used and diluted as follow:
  imidacloprid: 1000 mL of test solution was prepared diluting in water 20 μL of commercial formulation, containing 200 g/L of a.i., equivalent to 0.004 g of imidacloprid per liter of insecticidal solution;
  thiacloprid: 1000 mL of test solution was prepared diluting in water 24 μL of commercial formulation containing 480 g/L of a.i, equivalent to 0.012 g of thiacloprid per liter of insecticidal solution;

The compounds of Example 1 and Example 2 were formulated in the form of emulsified concentrate (EC).

The following amount of the EC formulations were added to the above described insecticidal solution of insecticide to have a final concentration of synergist equal to 1 g/L:

1.248 g of EC formulation containing 80.1% (w/w) of the compound of Example 2

1.242 g of EC formulation containing 80.5% (w/w) of the compound of Example 1

20 mL of test formulations were used to wet by dipping for 5" a small pea seedling (1-1.5 cm long). Seedlings were left at room temperature in a fume hood and allowed to dry for 15". After drying 10-15 apterous parthenogenetic females were moved to the seedling and allowed to settle. Mortality produced by pyrethroids was assessed 24 hours later. Mortality produced by neonicotinoids was assessed 48 hours later.

Three replicates were executed each composed by 2 subreplicates (seedlings) and 60-90 specimens were used per test formulation.

In parallel with the test, the mortality of aphids in an untreated control replicate (seedlings dipped in water) was determined using the same conditions and methods.

The maximum mortality rate allowed within the control group to consider the test representative was 10% after 24 hours and 15% after 48 hours. If above this value, the test was not considered representative and was repeated.

During the trials, no deviance has been noted.

The test conditions were as follows:

temperature: 21-22° C.

relative humidity: min. 60% light regime: 16 hour light/8 hours dark

The efficacy was calculated according the Abbott's formula:

$$\text{Efficacy \%} = \frac{\text{Mortality of treated sample(\%)} - \text{Mortality of control(\%)} \times 100}{(100 - \text{Mortality of control(\%)})}$$

The results are reported in Table 6

TABLE 6

Efficacy of the tested compounds

| Compound | Imidacloprid | thiacloprid |
|---|---|---|
| I (insecticide) | 14.2 | 36.242 |
| I + Compound of Example 2 | 72.0 | 94.872 |
| I + Compound of Example 1 | 71.6 | 94.435 |
| Compound of Example 2 | −20.3 | −20.3 |
| Compound of Example 1 | 23.8 | 23.8 |
| Control mortality | 14.5% | 14.5% |

The compounds of Example 1 and Example 2 show a very good efficacy in combination with the active ingredients imidacloprid and thiacloprid.

The invention claimed is:

1. A pesticide composition comprising at least one pesticidal active ingredient and at least one methylendioxyphenyl derivative compound of Formula (I)

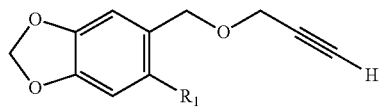

wherein $R_1$ is n-butyl or n-hexyl,
wherein the at least one pesticide active ingredient is selected from the group consisting of:
 a pyrethroid compound;
 a juvenile hormone-like substance;
 a neonicotinoid compound; and
 a carbamate compound; wherein the compound of Formula I has a synergist effect on the pesticide active ingredient.

2. The pesticide composition of claim 1, wherein $R_1$ is n-butyl.

3. The pesticide composition of claim 1, wherein the pyrethroid compound is cypermethrin.

4. The pesticide composition of claim 1, wherein the juvenile hormone-like substance is pyriproxyfen.

5. The pesticide composition of claim 1, wherein the neonicotinoid compound is thiacloprid or imidacloprid.

6. The pesticide composition of claim 1, wherein the carbamate compound is indoxacarb.

7. A pesticide formulation comprising the pesticide composition of claim 1 and a carrier.

8. A method for killing pests in close and open environments comprising applying the pesticide composition of claim 1 in said close and said open environments and killing said pests.

9. The method of claim 8 for killing pests in agriculture.

10. The method of claim 8, wherein the pests are selected from the group consisting of Hemiptera, Diptera, Blattaria, Thysanoptera, Isoptera, and Acarina.

11. A method of treating pediculosis in humans in need thereof with the pesticide composition of claim 1, said method comprising:
 applying said pesticide composition to said humans and treating said pediculosis.

12. A method for treating non-human mammal comprising applying to said non-human mammal the pesticide composition of claim 1.

* * * * *